US007041616B1

(12) United States Patent
Nenoff et al.

(10) Patent No.: US 7,041,616 B1
(45) Date of Patent: May 9, 2006

(54) ENHANCED SELECTIVITY OF ZEOLITES BY CONTROLLED CARBON DEPOSITION

(75) Inventors: Tina M. Nenoff, Albuquerque, NM (US); Steven G. Thoma, Albuquerque, NM (US); Mutlu Kartin, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 528 days.

(21) Appl. No.: 10/414,184

(22) Filed: Apr. 14, 2003

Related U.S. Application Data

(60) Provisional application No. 60/372,461, filed on Apr. 12, 2002.

(51) Int. Cl.
*B01J 29/06* (2006.01)
(52) U.S. Cl. .............................. 502/85; 502/64; 502/4; 502/71; 502/77; 502/79
(58) Field of Classification Search ...................... None
See application file for complete search history.

(56) References Cited

U.S. PATENT DOCUMENTS

| | | | | |
|---|---|---|---|---|
| 3,832,416 | A | * 8/1974 | Van Grinsven | ............. 585/831 |
| 4,547,613 | A | 10/1985 | Garwood et al. | |
| 4,570,029 | A | 2/1986 | Kulprathpanja et al. | |
| 6,191,331 | B1 | 2/2001 | Boldingh et al. | |
| 6,235,954 | B1 | * 5/2001 | Wu et al. | ................... 585/260 |
| 6,494,326 | B1 | 12/2002 | Nenoff et al. | |

OTHER PUBLICATIONS

Karger et al., "Controlled Coke Deposition on Zeolite ZSM5 and its Influence on Molecular Transport," *Appl. Catalysis 29*, 21 (1987).
Bonardet et al., "Use of NMR techniques for studying deactivation of zeolites by coking," *J. Molecular Catalysis A: Chemical 96*, 123 (1995).
Karge et al., "In-situ FTIR measurements of diffusion in coking zeolite catalysts," *Appl. Catalyst A: General 146*, 339 (1996).
Henriques et al., "Characterization of the Coke Formed During o-Xylene Isomerization over Mordenites at Various Temperatures," *J. Catalysis 172*, 436 (1997).
Yan et al., "Preparation of highly selective zeolite ZSM-5 membranes by a post-synthetic coking treatment," *J. Membrane Science 123*, 95 (1997).
Prasetyo et al., "Pore structure alteration of porous carbon by catalytic coke deposition," *Carbon 37*, 1909 (1999).
Leboda et al., "On the topography and morphology of carbon deposits prepared by pyrolysis of alcohols on the surface of silica gel," *Materials Chemistry and Physics 58*, 146 (1999).
Antes et al., "Chemistry and kinetics of chemical vapor deposition of pyrocarbon VII. Confirmation of the influence of the substrate surface area/reactor volume ratio," *Carbon 37*, 2031 (1999).
Pirngruber et al., "Deactivation of medium pore zeolite catalysts by butadiene during n-butene isomerization," *Microporous and Mesoporous Materials 38*, 221 (2000).
Cerqueira et al., "m-Xylene Transformation over a USHY Zeolite at 523 and 723 K: Influence of Coke Deposits on Activity, Acidity, and Porosity," *J. Catalysis 196*. 149 (2000).
Cerqueira et al., "Influence of coke on the acid properties of USHY zeolite," *Microporous and Mesoporous Materials 38*, 197 (2000).
Andy et al., "Molecular Modeling of Carbonaceous Compounds Formed Inside the Pores of FER Zeolite during Skeletal Isomerization of n-Butene," *J. Phys. Chem. B 104*(20), 4827 (2000).
Freitas et al., "Preparation of carbon molecular sieves for gas separations by modification of the pore sizes of activated carbons," *Fuel 80*, 1 (2000).

* cited by examiner

*Primary Examiner*—Christina Johnson
(74) *Attorney, Agent, or Firm*—Kevin W. Bieg

(57) ABSTRACT

A method for carbonizing a zeolite comprises depositing a carbon coating on the zeolite pores by flowing an inert carrier gas stream containing isoprene through a regenerated zeolite at elevated temperature. The carbonized zeolite is useful for the separation of light hydrocarbon mixtures due to size exclusion and the differential adsorption properties of the carbonized zeolite.

14 Claims, 5 Drawing Sheets

ENHANCED SELECTIVITY OF ZEOLITES BY CONTROLLED CARBON DEPOSITION

CROSS-REFERENCE TO RELATED APPLICATIONS

This application claims the benefit of U.S. Provisional Application No. 60/372,461, filed Apr. 12, 2002.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to the separation of light hydrocarbon mixtures and, in particular, to the separation of light hydrocarbons using carbonized nanoporous zeolites.

BACKGROUND OF THE INVENTION

Many commercial processes use gas purification and liquid-phase separations. In particular, the chemical and petroleum refining industries require materials that can effectively separate mixtures of hydrocarbon molecules and light gas molecules. Increasingly, these separations are accomplished with molecular sieves, including porous crystalline aluminosilicates (zeolites), that contain pores of molecular dimensions and can therefore exhibit selectivity according to the effective size of a liquid or gas molecule. As a result, zeolites can be used for the separation of mixtures of molecules of varying size.

The effectiveness of a zeolite for separation is determined by the product of its permeability and selectivity. Permeability describes the hydraulic transport resistance of a fluid and is measured by the transmembrane flux per unit pressure difference across a membrane. Selectivity measures the ability of the zeolite to preferentially separate or retain a species from a mixture. Selectivity of a zeolite can be enhanced by tailoring the geometry of the pore (i.e., to alter size exclusion) and by modifying the pore surfaces or acidity of the framework to effect adsorption.

Previous commercial separations of similar hydrocarbon molecules have used either cryogenic distillation or sieving by simple size exclusion. Cryogenic distillation is very energy intensive and pollution producing. Furthermore, it is a non-regenerative process. Separation processes using bulk or membrane zeolites have primarily relied on only size exclusion to achieve physical separation of molecules. Size exclusion alone is inadequate for separations of many commercially important hydrocarbons, such as isoprene, from similar boiling point and similar sized molecules, such as n-pentane, in commercial mixtures. Thus, there is a need to further enhance the selectivity of zeolites by modifying their adsorptive property in order to change the interaction of the diffusing molecules with the internal surfaces of the zeolite structure.

Both bulk and membrane zeolites can be used for molecular separations. Bulk zeolites have the problem of trapping the bulkier molecule in the zeolite pores, thereby generally restricting their use to batch or semi-batch separation processes. Zeolite membranes offer the possibility of continuous separations and zeolite regeneration. However, the synthesis of quality zeolite membranes has been difficult. Because self-supporting zeolite membranes lack durability, most membranes are hydrothermally grown on substrates having pores much larger than the nanoporous zeolite. The as-grown zeolite films tend to have many microdefects or improper pore orientation, which hinder the separation characteristics of the zeolite.

Recently, suitable thin-film membranes that are robust, thermally stable, and have high selectivity with good throughput have been disclosed by Nenoff, et al. in U.S. Pat. No. 6,494,326, which is incorporated herein by reference. These membranes have been fabricated by a combination of growth of zeolite crystallites on a substrate followed by embedding the crystallites in a densified sol-gel product layer, thereby filling in the micropores that otherwise reduce selectivity of the membrane. The zeolite crystals grown inside a membrane tube or on a membrane disk are chosen so their crystal structure allows the passage of gases or molecules of a particular size.

Due to their high acidity and chemical reactivity, many zeolites are not suitable for hydrocarbon separations. Rather, their acidic properties and shape selectivity make zeolites more useful as catalysts for hydrocarbon cracking and isomerization in many refining and petrochemical processes. However, coking from the cracked hydrocarbons is known to deactivate acid sites, resulting in loss of catalytic activity and fouling. Coke generally comprises a mixture of partially decomposed hydrocarbon molecules. See, e.g., U.S. Pat. No. 6,191,331 to Boldingh; U.S. Pat. No. 4,547,613 to Garwood, et al.; C. A. Henriques et al., *J. Catalysis* 172, 436 (1997); G. D. Pirngruber et al., *Microporous and Mesoporous Materials* 38, 221 (2000); and H. S. Cerqueira et al., *J. Catalysis* 196, 149 (2000).

Various post-synthetic coking treatments have been used to "caulk" the microdefects of zeolites with carbonaceous deposits for separations. See, e.g., Y. Yan et al., *Journal of Membrane Science* 123, 95 (1997). This coking process uses a large aromatic hydrocarbon to fill the microdefects and thereby enhance selectivity, however, at the expense of reduced permeability. Although selectivity was restored, large reductions in permeability have been observed with these "caulked" membranes. It is unlikely that the hydrocarbon molecules enter the zeolite nanopores during the caulking treatment. Therefore, the resulting enhanced selectivity is likely due to size exclusion, rather than selective adsorption.

Therefore, a need remains for the controlled modification of sorptive capacity and pore size of zeolites used for separations. Coking of zeolites provides a means to deactivate the acid sites that cause hydrocarbon cracking, and may provide a means for hydrocarbon separation, if the weak bonding sites required for selective adsorption can be retained. Therefore, the adsorptive properties and selectivity of zeolites may be modified by controlled deposition of carbon into the void volume of the zeolite structure. The present invention provides a method for the controlled carbonization of zeolites. The present invention further provides a method for light hydrocarbon separations using the carbonized zeolite. The method combines the advantages of separations based on variations in molecule size with those based on the differences in molecular adsorption properties. This combination enables effective molecular separations that are not attainable by either size exclusion or differential adsorptivity alone.

SUMMARY OF THE INVENTION

A present invention is directed to a method for carbonizing a zeolite, comprising flowing an inert gas through the zeolite at a first elevated temperature to regenerate the pores of the zeolite; and flowing an inert gas stream comprising isoprene through the regenerated zeolite at a second elevated temperature, wherein the regenerated zeolite has a pore size greater than the kinetic diameter of the isoprene molecules, thereby depositing a carbon coating in the pores of the regenerated zeolite.

The present invention further comprises a method for separating a light hydrocarbon mixture using the carbonized zeolite, the method comprising exposing a feed gas stream comprising a mixture of at least two light hydrocarbons to the carbonized zeolite, thereby providing a permeate stream enriched in one of the light hydrocarbons of the mixture.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

The present invention comprises a method for enhancing the selectivity of a zeolite by controlled carbonization using isoprene. The present invention further comprises a method for separating light hydrocarbons using the carbonized zeolite. The methods can be applied to all types of zeolites either in bulk form or grown as membrane thin films. Supported membranes of crystalline nanoporous zeolites can be synthesized by hydrothermal methods, as described by Nenoff et al. Bulk crystalline nanoporous zeolites can be obtained commercially, including aluminosilicate zeolites, ZSM-22, ZSM-5, zeolite β, zeolite-L, and zeolite-Y. These zeolites tend to be chemically reactive, due to their high acidity. The relative acidities of the zeolites depends on the zeolite structure, Si:Al ratio, type of acid site, and the strength of the site as determined by the charge-neutralizing cation (e.g., $NH_4^+$, $Na^+$, $K^+$, or $Cs^+$). These zeolites have a very defined pore structure with pore size generally less than 10 Å (e.g., ranging from 4.6 to 7.4 Å, respectively). In general, the pore size of the zeolite should be greater than the kinetic diameter of the isoprene molecule to achieve interior carbon deposition and achieve acid-site deactivation.

The chemical reactivity can be modified by the controlled deposition of carbon on the pores of these zeolites. This controlled deposition allows for enhanced selective separation of a hydrocarbon molecule from a mixture of chemically similar hydrocarbon molecules. The carbonized zeolites are particularly useful for separation of the difficult-to-separate light hydrocarbons (i.e., C4/C5/C6 hydrocarbons). The carbonized zeolites enable enhanced selectivity due to the combination of (1) molecular sieving based on molecule size and (2) preferential adsorption based upon carbon-modified adsorption sites (quantitatively modified sorptive capacity), generally inside the zeolite channels.

Prior to a separation process, the zeolite can be regenerated by heat-treatment in a flowing inert gas, followed by the carbon deposition procedure. The regeneration removes ancillary pore-blocking molecules, such as water. The regenerated zeolite can then be carbonized by exposure to an inert carrier gas stream containing controlled amounts of isoprene or n-pentane/isoprene mixtures at elevated temperature. The isoprene concentration, inert gas flow rate, exposure time, and temperature can be modified to control the properties of the carbon deposited. Following carbon deposition, the zeolite can be maintained at an elevated temperature under flowing inert gas until all residual (non-coked) hydrocarbon molecules are fully decomposed to elemental carbon. After cooling, the carbonized zeolite, either in bulk or membrane form, can be used for separation of a hydrocarbon mixture.

Figure 1:
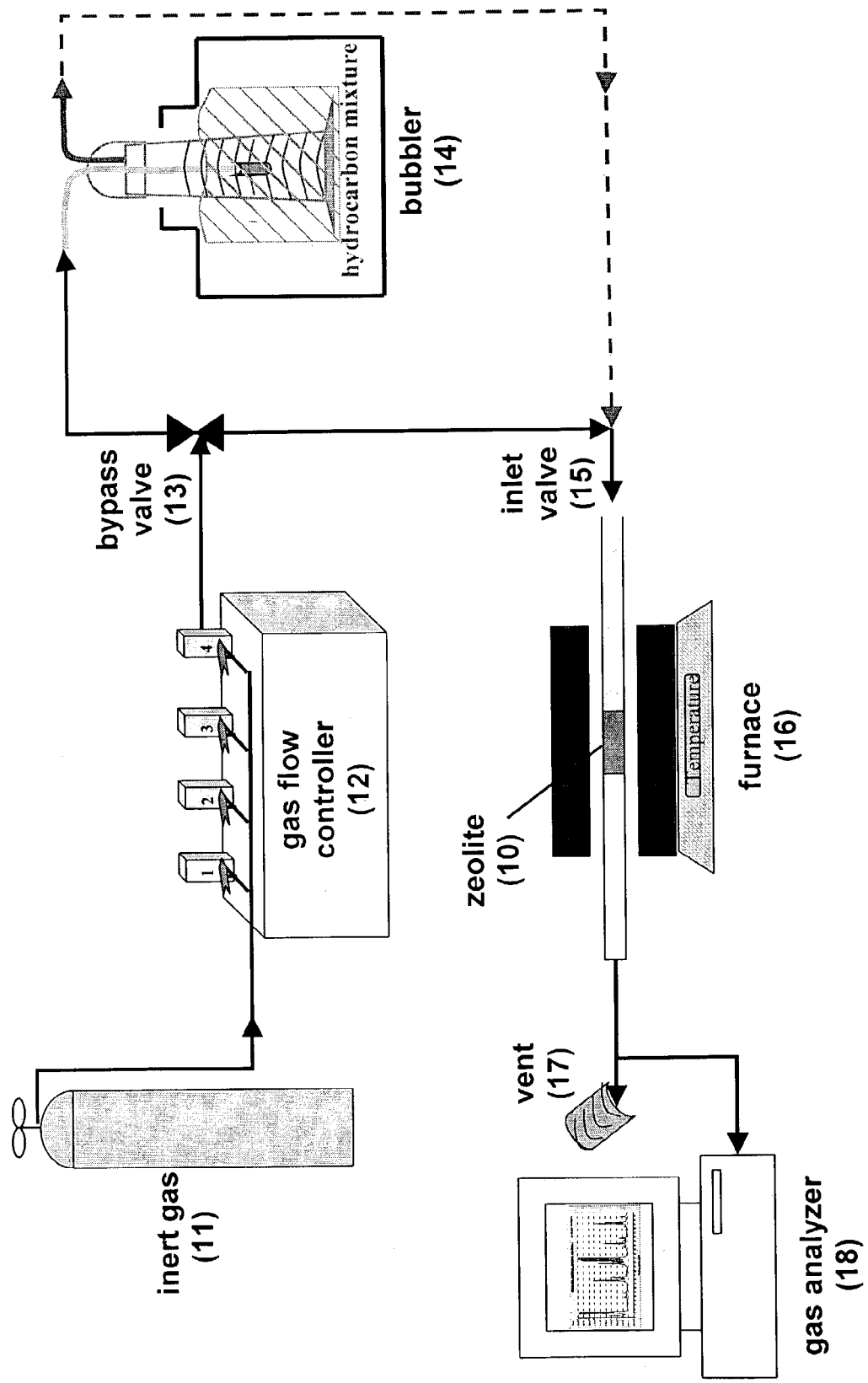
FIG. 1 is a schematic illustration of an apparatus for the regeneration and carbonization of a zeolite.

In FIG. 1 is shown an apparatus that can be used for the regeneration and carbonization of a zeolite 10. The apparatus comprises a source of inert gas 11, gas flow controller 12, bypass valve 13, hydrocarbon-containing bubbler 14, inlet valve 15, furnace 16, vent 17, and gas analyzer 18. The source of inert gas 11 can be a compressed gas cylinder containing helium, nitrogen, or other inert gases. The gas flow controller 12 can be a digital gas flow regulator for controlling the inert gas flow rate. The bypass valve 13 allows the inert gas to be directed into the bubbler 14 or the furnace 16. The furnace 16 can be a high temperature tube furnace or the like. The gas analyzer 18 can be a mass spectrometer.

The zeolite 10 can be regenerated in the high temperature furnace 16 by flowing inert gas 11 through the zeolite 10 until the ancillary pore-blocking molecules are no longer observed in the effluent. The inert gas 11 is directed by the bypass valve 13 and inlet valve 15 into the furnace 16 that contains the zeolite 10 to be regenerated. Typically, the inert gas flow rate can be about 10 to 20 SCCM. Preferably, the furnace 16 is maintained at a temperature of 400 to 700° C. during the zeolite regeneration. The effluent from the furnace 16 can be vented through vent 17 or analyzed by gas analyzer 18 to monitor the removal of the pore-blocking molecules.

The regenerated zeolite 10 can be carbonized by flowing a zeolite-containing gas stream over the regenerated zeolite 10 at an elevated temperature for an extended period of time. For carbonization, the inert gas 11 is directed by the bypass valve 13 into the bubbler 14. The inert gas 11 is bubbled through a liquid hydrocarbon mixture containing isoprene to pick up and carry the hydrocarbon vapor via the inlet valve 15 into the furnace 16 containing the regenerated zeolite 10. The liquid hydrocarbon mixture in the bubbler 14 preferably comprises greater than 20% isoprene in n-pentane. For liquid n-pentane/isoprene mixtures, the bubbler 14 is preferably chilled at about 0° C. The furnace 16 is preferably maintained at a temperature of about 400 to 700° C. while the zeolite 10 is being carbonized. The zeolite 10 can be exposed to the hydrocarbon vapor at this elevated temperature for about 1 to 4 hours. The zeolite 10 can be then be maintained at the elevated temperature under flowing inert gas until no hydrocarbon molecules are detected by the gas analyzer 18. The furnace 16 can then be cooled down.

Figure 2:
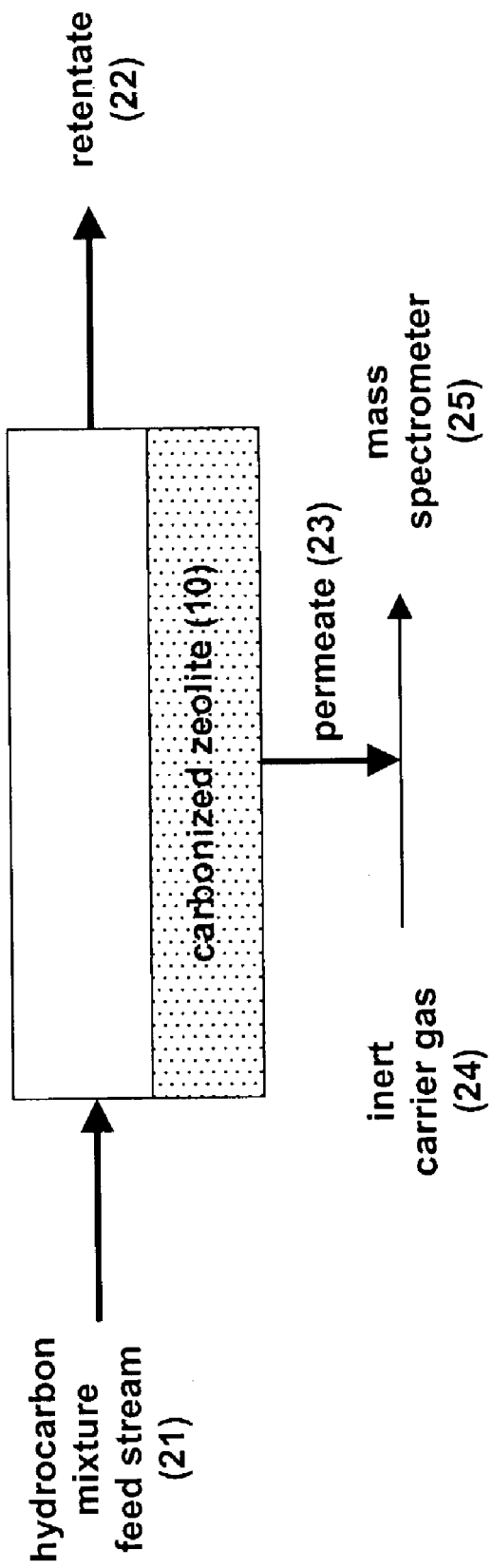
FIG. 2 is a schematic illustration of an apparatus for separating a light hydrocarbon mixture using a carbonized zeolite membrane.

A hydrocarbon can be separated from a hydrocarbon mixture using the apparatus shown in FIG. 2. A feed stream 21 comprises the hydrocarbon mixture to be separated. The feed stream 21 flows over a membrane or packed bed of the carbonized zeolite 10. The carbonized zeolite 10 selectively separates the hydrocarbon from the other hydrocarbons in the mixture, yielding a permeate stream 23 enriched in the hydrocarbon and a retentate stream 22 depleted in the hydrocarbon. The permeate stream 23 can be carried by inert gas 24 into a mass spectrometer 25 for analysis.

EXAMPLE 1

Regeneration of Zeolite-L

A bulk sample of zeolite-L was regenerated using the apparatus shown in FIG. 1. Either a stainless steel or a quartz tube was used in the tube furnace. The 3/8" OD stainless steel tube or 10 cm OD quartz tube was washed with water and acetone and the tube was dried in a furnace at 1000° C. for about 2–3 hrs. One end of the tube was then packed with quartz wool. The tube was filled with approximately 1 g. of zeolite-L. The other end of the tube was buffered with quartz wool and the tube was shaken to avoid plugging. Both ends of the tube were tightened with swage locks. One end of the tube was connected to helium gas flow and the other end of the tube was left unlocked. A digital gas flow regulator was used to adjust the helium flow rate into the tube. The unlocked end was directed to the vent. A thermocouple was inserted through the unlocked end of the tube. The effluent from the downstream end of the tube was sampled by a mass spectrometer and then vented to a silicon oil bubbler. No atmospheric (i.e., contaminant) gases could enter the apparatus. The stainless steel or quartz tube was placed into the programmable tube furnace. The bypass valve and the inlet valve were directed into the furnace. The helium gas was then flowed through the zeolite-loaded tube. The zeolite-L was regenerated by ramping the furnace at a rate of 20° C./min up to 700° C. for 4 hrs under a 10 SCCM helium flow. The regeneration of the zeolite-L was complete when ancillary pore-blocking molecules were no longer observed in the effluent by the mass spectrometer.

The high temperature exposure regenerates the active acid sites in the zeolite. The presence of active sites can be determined by temperature-programmed desorption from the regenerated zeolite after exposure to a hydrocarbon mixture. The hydrocarbon mixture can be flowed over the carbonized zeolite at low temperature (i.e., 50° C.) in the tube furnace. Any adsorbed hydrocarbon species can be subsequently desorbed by heating the exposed zeolite to a high temperature. The desorption of any adsorbed hydrocarbons indicates the presence of active acid sites in the regenerated zeolites.

Temperature-programmed desorption of regenerated zeolites was performed using the apparatus shown in FIG. 1. The tube furnace containing the zeolite was cooled down to about 50° C. following regeneration. Helium flow was directed through the bubbler, containing an 80/20 (vol/vol) n-pentane/isoprene mixture, which was chilled at 0° C. The hydrocarbon-containing helium gas from the bubbler was allowed to flow over the regenerated zeolite for 30 to 60 minutes until a steady state was achieved. The bypass valve was then switched, and pure helium was allowed to flow through the zeolite at 50° C. until no n-pentane or isoprene was detected in the effluent stream. The adsorption of the n-pentane or isoprene by the zeolite was then detected by temperature ramping the furnace by 20° C./min to 700° C. Desorption of the adsorbed n-pentane or isoprene was identified via a mass spectrometer and recorded as a function of temperature.

Figures 3A, 3B:
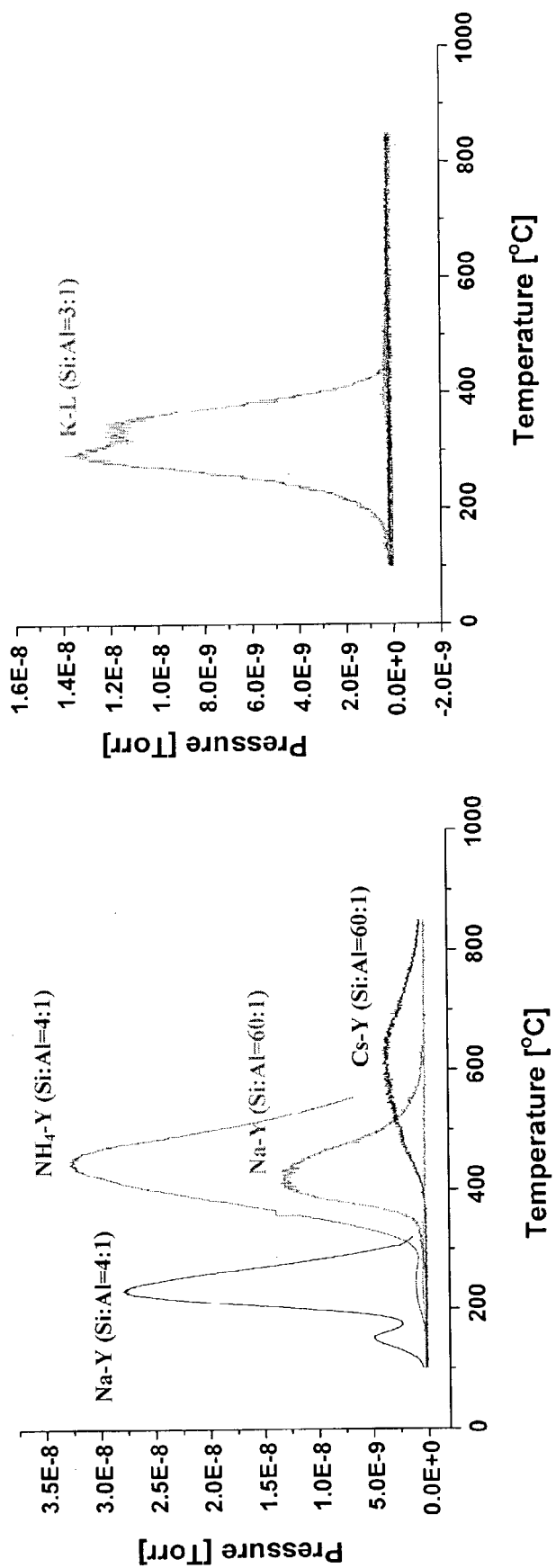
FIGS. 3A and 3B show the temperature-programmed desorption of n-pentane and isoprene from the active acid sites of regenerated zeolites.

In FIGS. 3A and 3B are shown the temperature-programmed desorption results for the zeolite-L (K—L, with a Si:Al ratio of 3:1) and several other zeolite-Ys (i.e., Na—Y (Si:Al=4:1), Na—Y (Si:Al=60:1), Cs—Y (Si:Al=60:1), and $NH_4$—Y (Si:Al=4:1)). The area of a desorption peak is proportional to the amount of each hydrocarbon specie desorbed. Species that come off at lower temperatures are adsorbed less strongly than species that come off at higher temperatures. Two peaks for the same species indicates that there are two different strength active sites. From these results, it can be seen that zeolite-L preferentially adsorbs branched hydrocarbons (e.g., isoprene) and zeolite-Y preferentially adsorbs linear hydrocarbons (e.g., n-pentane).

EXAMPLE 2

Carbonization of Zeolite-L

The regenerated zeolite-L was carbonized using the same apparatus shown in FIG. 1. While the furnace containing the regenerated zeolite-L described above was at 700° C., the helium flow was directed through a bubbler. The bubbler, containing a 80/20 (vol/vol) n-pentane/isoprene, was chilled at 0° C. The n-pentane/isoprene mixture was prepared by measuring the corresponding volume ratio of each hydrocarbon and putting the hydrocarbons into the glass cylindrical 250 ml bubbler. The bubbler was capped by parafilm. The top ends of the bubbler were swage locked and the bubbler was allowed to cool for about 20 min. In FIG. 1, the bypass valve was in the open position and the inlet valve was directed to the tube furnace. This allowed the helium carrier gas to flow into the bubbler and thereby carry the n-pentane/isoprene mixture to the furnace. The hydrocarbon-containing helium gas was flowed over the zeolite-L for 1 to 4 hrs. A P vs. T plot was monitored with the mass spectrometer. The bubbler was then switched off. Pure helium was allowed to flow through the zeolite at elevated temperature (e.g., 700° C. for 1 hr.) until no hydrocarbon molecules are detected via mass spectrometry. The furnace was then cooled down to 50° C.

The effect of carbonization on the acid-site deactivation of the zeolite can be assessed with temperature-programmed desorption, as described above. A hydrocarbon mixture can be flowed over the carbonized zeolite at low temperature (e.g., 50° C.) in the tube furnace. Any adsorbed hydrocarbon species will be subsequently desorbed by heating the exposed zeolite to a high temperature.

Figures 4A, 4B:
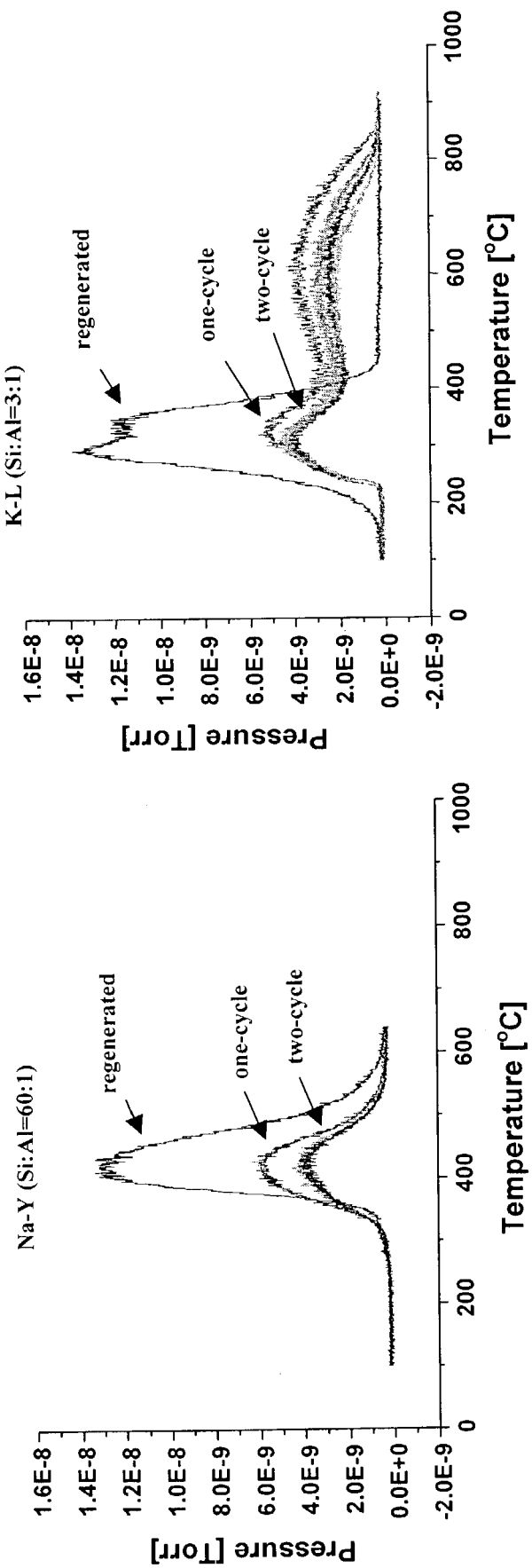
FIGS. 4A and 4B show the temperature-programmed desorption of n-pentane and isoprene from the acid-site deactivated zeolites.

FIGS. 4A and 4B show the temperature-programmed desorption results for a zeolite-Y (Na—Y (Si:Al=60:1)) and zeolite-L (K—L (Si:Al=3:1)), respectively, after exposure to an n-pentane/isoprene mixture. FIGS. 4A and 4B show n-pentane desorption from the zeolite-Y and isoprene desorption from the zeolite-L, respectively, after regeneration and after one or more carbonization cycles. The concentration of n-pentane or isoprene in the high-temperature effluent was significantly reduced after only one carbonization cycle. This indicates that n-pentane or isoprene absorption was significantly reduced by the carbonization. Therefore, carbonization is effective in deactivating the active sites of the regenerated zeolites. Furthermore, the lack of hydrogen in the effluent indicated that no hydrocarbons were decomposed and hence irreversibly adsorbed.

EXAMPLE 3

Separation of an n-Pentane/Isoprene Mixture with Carbonized Zeolite-L

A light hydrocarbon mixture can be separated using the carbonized zeolite in the apparatus shown in FIG. 2. A column was packed with the carbonized zeolite-L prepared according to the carbonization procedure described above. A 80/20 n-pentane/isoprene mixture was chilled to 0° C. and flowed across the feed end of the column. Pure helium was flowed across the permeate end of the column and the permeate stream was analyzed by a mass spectrometer.

Figure 5:
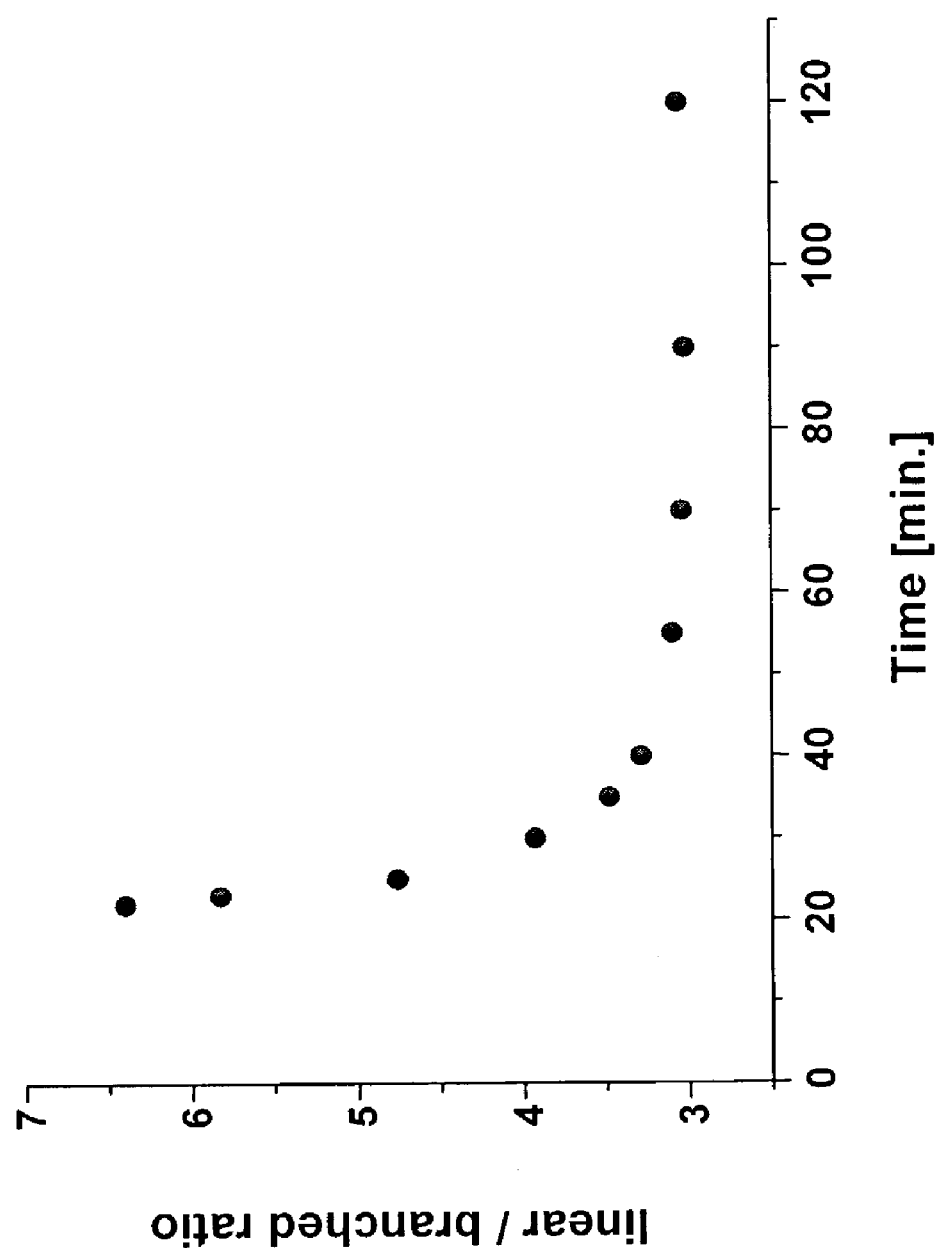
FIG. 5 shows the separation of an n-pentane/isoprene mixture using a packed bed column comprising carbonized zeolite.

In FIG. 5 is shown the ratio of the linear hydrocarbon (i.e., n-pentane) to the branched hydrocarbon (i.e., isoprene) in the permeate stream. The permeate stream was enriched to over 6:1 n-pentane/isoprene by passing the hydrocarbon mixture through the carbonized zeolite-L column. After about 20 minutes, the carbonized zeolite-L became saturated with isoprene and the concentration of the permeate stream returned to 3.05:1 n-pentane/isoprene, the ratio resulting from molecular sieving based on molecular size only. These results show that, prior to saturation, the carbonization enhances the selectivity of the zeolite due to preferential adsorption based upon carbon-modified adsorption sites.

It will be understood that the above description is merely illustrative of the applications of the principles of the present invention, the scope of which is to be determined by the claims viewed in light of the specification. Other variants and modifications of the invention will be apparent to those of skill in the art.

We claim:

1. A method for carbonizing a zeolite, comprising:
   flowing an inert gas through the zeolite at a first elevated temperature to regenerate the pores of the zeolite; and
   flowing a gas stream comprising isoprene through the regenerated zeolite at a second elevated temperature, wherein the regenerated zeolite has a pore size greater than the kinetic diameter of the isoprene molecules, thereby depositing a carbon coating in the pores of the regenerated zeolite.

2. The method of claim 1, wherein the zeolite comprises ZSM-22, ZSM-5, zeolite β, zeolite-L, or zeolite-Y.

3. The method of claim 1, wherein the zeolite comprises a charge-neutralizing cation $NH_4^+$, $Na^+$, $K^+$, or $Cs^+$.

4. The method of claim 1, wherein the zeolite comprises bulk zeolite.

5. The method of claim 1, wherein the zeolite comprises a zeolite membrane.

6. The method of claim 1, wherein the first elevated temperature is greater than 400° C.

7. The method of claim 1, wherein the second elevated temperature is greater than 400° C.

8. The method of claim 1, wherein the gas stream comprises a hydrocarbon mixture.

9. The method of claim 8, wherein the hydrocarbon mixture comprises n-pentane and isoprene.

10. The method of claim 8, wherein the hydrocarbon mixture comprises greater than 20% isoprene.

11. The method of claim 1, further comprising flowing a feed stream comprising a mixture of at least two light hydrocarbons over the carbonized zeolite, wherein the carbonized zeolite selectively separates one of the at least two hydrocarbons from the mixture to yield a permeate stream enriched in the one hydrocarbon.

12. The method of claim 11, wherein the at least two light hydrocarbons comprise C4, C5, or C6 hydrocarbons.

13. The method of claim 11, wherein the at least two light hydrocarbons comprise at least one branched hydrocarbon and at least one linear hydrocarbon.

14. The method of claim 11, wherein the at least two light hydrocarbons comprise n-pentane and isoprene.

* * * * *